United States Patent
Qu et al.

(10) Patent No.: US 12,130,939 B2
(45) Date of Patent: Oct. 29, 2024

(54) SYSTEM AND METHOD FOR CONSENT MANAGEMENT

(71) Applicant: KONINKLIJKE PHILIPS N.V., Eindhoven (NL)

(72) Inventors: Jin Qu, Shanghai (CN); Xin Ge, Shanghai (CN); Peter Petrus van Liesdonk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 307 days.

(21) Appl. No.: 17/419,740

(22) PCT Filed: Dec. 31, 2019

(86) PCT No.: PCT/EP2019/087186
§ 371 (c)(1),
(2) Date: Jun. 30, 2021

(87) PCT Pub. No.: WO2020/141170
PCT Pub. Date: Jul. 9, 2020

(65) Prior Publication Data
US 2022/0067196 A1    Mar. 3, 2022

(30) Foreign Application Priority Data
Jan. 4, 2019  (WO) ................ PCT/CN2019/070383

(51) Int. Cl.
*G06F 21/62*    (2013.01)
(52) U.S. Cl.
CPC ............................ *G06F 21/6245* (2013.01)

(58) Field of Classification Search
None
See application file for complete search history.

(56) References Cited

U.S. PATENT DOCUMENTS

| | | | |
|---|---|---|---|
| 7,269,853 B1 * | 9/2007 | Dunn | H04L 63/102 726/27 |
| 2011/0119290 A1 * | 5/2011 | Dhoble | G16H 80/00 707/769 |
| 2012/0331567 A1 * | 12/2012 | Shelton | G06Q 10/00 726/28 |
| 2013/0086645 A1 | 4/2013 | Angal | |
| 2014/0026194 A1 * | 1/2014 | Smith | G06F 21/6245 726/4 |
| 2016/0188805 A1 | 6/2016 | Awaragi | |
| 2018/0082023 A1 | 3/2018 | Curbera | |
| 2018/0276341 A1 | 9/2018 | Boutrs | |
| 2019/0005210 A1 * | 1/2019 | Wiederspohn | G06F 21/31 |
| 2019/0166133 A1 * | 5/2019 | Frederick | H04L 9/3239 |
| 2019/0348158 A1 * | 11/2019 | Livesay | G16H 10/60 |

OTHER PUBLICATIONS

International Search Report for PCT/EP2019/087186 filed Dec. 31, 2019.

* cited by examiner

*Primary Examiner* — Piotr Poltorak
*Assistant Examiner* — Felicia Farrow

(57) ABSTRACT

The invention provides a consent management system for managing a user's consent for a plurality of services. The system includes a consent management unit adapted to register a plurality of services to a user and obtain user consent information associated with the user. The consent management unit is further adapted to control consent operation of the plurality of services registered to the user, based on user consent information associated with the user.

11 Claims, 3 Drawing Sheets

SYSTEM AND METHOD FOR CONSENT MANAGEMENT

CROSS-REFERENCE TO PRIOR APPLICATIONS

This application is the U.S. National Phase application under 35 U.S.C. § 371 of International Application No. PCT/EP2019/087186, filed on Dec. 31, 2019, which claims the benefit of International Application No. PCT/CN2019/070383, filed on Jan. 4, 2019. These applications are hereby incorporated by reference herein.

FIELD OF THE INVENTION

The invention relates to the field of data privacy and user consent, and in particular the field of consent management.

BACKGROUND OF THE INVENTION

A user's consent is typically required by privacy regulations to record a data subject's privacy preference on how to process the user's consent information, for example the user's personal data. Examples of a data subject include a user of a service, a patient of a medical service, or an individual with a corresponding recorded information set.

Normally, for a user to register with a conventional service, the user provides consent for the service to process his/her personal data. The service may then store information about this consent as a legal basis to process the user's consent information. If privacy terms of the service are updated, the service is typically required to notify the user (e.g. through an email communication or directly through the service) in order to seek the user's consent once again.

A user may be registered with multiple services. These services typically store the user's consent information and the user's consent in order to process the consent information. For services that are frequently accessed and used by the user, notifications regarding updates (e.g. to the service privacy notice) may be readily available. Further, requests for input required by the user (e.g. the user's agreement to a privacy notice update) can be regularly delivered to and identified by the user. However, for services that the user does not frequently access and/or use, it can be difficult to transparently and efficiently notify the user and receive the user's input for such requirements described above. This affects the efficiency of how the service is used and consequently the efficiency of the service itself.

Conventionally, a user is required to access each of the different services to manage his/her consent and corresponding user consent information for each of the services. This approach requires the user's time to complete a repetitive task, resulting in a tedious and inefficient process.

There therefore remains a need to optimize the process of managing a user's consent and corresponding user consent information required by privacy relevant regulations across multiple services that the user is registered with.

SUMMARY OF THE INVENTION

The invention is defined by the claims.

According to examples in accordance with an aspect of the invention, there is provided a consent management system for managing a user's consent for a plurality of services, the system comprising: a consent management unit adapted to: register a plurality of services to a user; obtain user consent information associated with the user; and control consent operations of the plurality of services registered to the user, based on user consent information associated with the user.

Proposed are concepts for managing a user's consent for a plurality of services. One such concept may provide a centralised (or intermediary) consent management system that acts as a unified interface for a user to access their consent-related preferences and/or permissions. The consent management system can assign/link multiple services to the user, and this may then enable the system to centrally control the user's consent-relevant business for the multiple services. In this way, a single point or node may be provided for managing the user's consent for multiple services in a transparent and efficient manner.

It is proposed to provide a single resource or service that manages a user's consent and corresponding user consent information for a plurality of services registered to a user. The single resource or service enables the user to access all user consent information relevant to the plurality of registered services. The user can manage and control the user's consent-relevant business for a plurality of registered services from a single centralised resource or service.

This may allow for improved efficiency of communication between the user and the plurality of services registered to the user. This may result in improved transparency and efficiency in managing a user's consent and user consent information for a plurality of services. Thus, unlike conventional approaches, the user may not be required to access multiple services in order to retrieve and manage the user's consent and user consent information corresponding to each service. Instead, the user can access and manage the user's consent and user consent information through a centralised system.

In an embodiment, the consent operations may comprise operations employing data privacy preference information associated with the user. In this way, the consent management system may be enabled to manage the user's consent and handle the user's rights on data privacy for services registered to the user.

For example, the operations employing data privacy preference information may comprise at least one of: responding to a user request from the user; responding to a service request from the plurality of services; and determining if the user consent information associated with the user is consistent with data access requirements of a service. In this way, the consent management system may be enabled to manage requests from both the user and the registered services. Thus, the user may have access to all service requests in a unified interface. This may remove the need for the user to access multiple separate services in order to receive and manage service requests.

The user consent information may be the user's privacy preference on how a service can process data corresponding to the user. For example, the user consent information includes a user's privacy settings, which may define preferences set by the user on how the user's data is gathered, processed, disclosed, handled, and/or managed by a service. The user consent information may further comprise at least one of: the user's privacy preference on the purpose for the processing of a user's data, the user's privacy preference on how the user's data is shared by the service (e.g. who it is shared with, when it is shared, and/or why it is shared), the user's privacy preference on receiving communications from the service, the user's privacy preference on a service's reporting process for a data breach, the user's privacy preference on a service's data retention policy, and the user's privacy preference on how the user's data is stored by the service.

The user's data may include at least one of: personal details corresponding to the user, information that can be used to identify the user, content provided by a user to a service, and information in or about the content that a user provides to a service (e.g. metadata). For example the user's data includes, but is not limited to, at least one of: the user's name, address, date of birth, marital status, contact information, ID issue, and expiry date, financial records, credit information, medical history, travel information, internet usage information, and intentions to acquire goods and services.

In this way, the consent operations controlled by the consent management unit may employ the user consent information described in the embodiments above.

Further, the user may be able to provide user requests for multiple services from a unified interface, improving the efficiency of submitting user requests. This may be particularly beneficial for a service that the user does not frequently access, as the system may improve the efficiency of communication between the user and the service.

The consent management system may be enabled to perform an automatic comparison between the user consent information and the data access requirements of the service in order to determine a consistency between the two. This may mitigate a need for the user to manually complete the comparison and may reduce the risk of human error in the comparison (e.g. due to overlooking a detail).

In an embodiment, the consent management unit, in responding to a user request from the user, may be adapted to: receive the user request from the user; request the plurality of services to complete the user request; and synchronize the user consent information between the consent management system and the plurality of services. In this way, the consent management system may enable the user to provide the user request for multiple services through one unified interface (the consent management system).

Further, the consent management system may reduce a risk of inconsistencies between the user consent information registered at the consent management system and the user consent information registered at the plurality of services.

In an embodiment, the user request may comprise one or more of: updating the user's consent; revoking the user's consent; correcting the user consent information; and deleting the user consent information. Accordingly, the consent management system may be enabled to manage and control the user's consent and corresponding user consent information (e.g. data linked to the user's consent) at multiple services, based on the request provided by the user.

In an embodiment, the consent management unit, in responding to a service request, may be adapted to: receive the service request from the plurality of services; notify the user of an update; receive a user response; and respond to the plurality of services according to the user response. The consent management system may thus enable the user to access all notifications received from the services in a unified interface, thereby improving the efficiency of communication between the services and the user. The user may further provide a response, corresponding to the service request, to the plurality of services. For example, the consent management system may provide the response, submitted by the user, to multiple services.

In an embodiment, the service request may comprise one or more of: a privacy notice; and updating the user's consent. The consent management system may therefore enable the user to be notified of updates from multiple services that may require the user's attention or input.

In an embodiment, the system may further comprise a data storage unit adapted to store the user consent information associated with the user. The consent management system may thus be enabled to access the user consent information and synchronize the information between the system and the registered services.

In an embodiment, the consent management unit, in registering the plurality of services to the user, may be adapted to: delegate the consent management unit to manage the user's consent; generate a token; and register the plurality of services to the user using the token. The token may be unique to the user. This may enable the consent management system to generate the information required for the process of registering only once. Thus, the consent management system may implement an efficient method of registering multiple services to the user.

For instance, in an embodiment, the token may comprise at least one of: a consent management system network address; a service network address; the user request; a timestamp; a validation period for the user consent; and a digital signature. In this way, the generated token may contain all information required for registering the plurality of services to the user. The token may be used more than once, mitigating the need for the consent management system to repeatedly generate the information when required.

In an embodiment, the system may further comprise a user interface unit adapted to display one or more of: a list of the plurality of services; notifications from the plurality of services; a list of entries of consent; and a list of user rights. The unified interface provided by the consent management system may therefore be a user interface unit. This may provide the user with access to a summary of information relevant to the services and the user's consent, improving the efficiency of communicating the information.

In an embodiment, the system may be a blockchain-based consent management system adapted to record one or more of: the user consent information; the privacy notice from the plurality of services; the user request; and the service request. Thus, the data used by the consent management system may be decentralized and alterations to the data may require a consensus of a network corresponding to the block-chain based consent management system. This may reduce the risk of retroactive alterations to the data.

In an embodiment, the consent management unit may be further adapted to receive the user consent information.

According to examples in accordance with an aspect of the invention, there is provided a computer program product for managing a user's consent for a plurality of services, the computer program product comprising a computer readable storage medium having program instructions embodied therewith, the program instructions executable by a processing unit to cause the processing unit to perform a method comprising: registering a plurality of services to the user; obtaining user consent information associated with the user; and controlling consent operations of the plurality of services registered to the user, based on user consent information associated with the user.

According to examples in accordance with an aspect of the invention, there is provided method for managing a user's consent for a plurality of services, the method comprising: registering a plurality of services to the user; obtaining user consent information associated with the user; and controlling consent operations of the plurality of services registered to the user, based on user consent information associated with the user.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
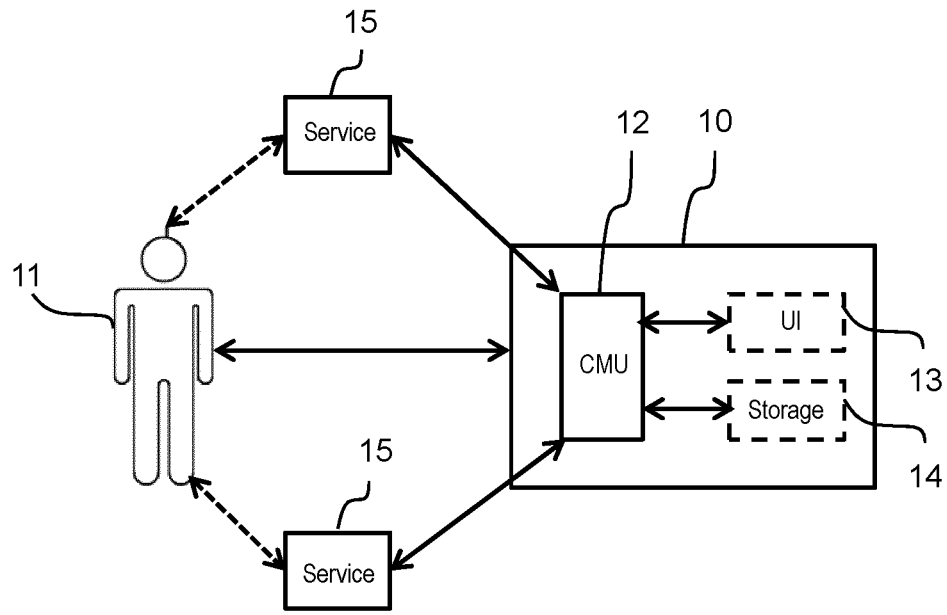
FIG. 1 is a simplified block diagram of a system for managing a user's consent for a plurality of services according to an embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a consent management system for managing a user's consent for a plurality of services. The system includes a consent management unit adapted to register a plurality of services to a user and obtain user consent information associated with the user. The consent management unit is further adapted to control consent operation of the plurality of services registered to the user, based on user consent information associated with the user.

FIG. 1 shows a system 10 for managing a user's consent for a plurality of services 15.

The system 10 acts as a unified interface between the plurality of services 15 and the user 11. The system 10 is in direct communication with the plurality of services 15 and enables the user 11 to access consent-relevant business. Thus, an indirect path of communication is achieved between the user 11 and the plurality of services 15 via the system 10. Indirect paths of communication are indicated in FIG. 1 using dashed arrows. Direct paths of communication are indicated in FIG. 1 using solid arrows.

The system 10 includes a consent management unit 12, a user interface unit 13 and a data storage unit 14.

The consent management unit 12 is adapted to register a plurality of services 15 to a user 11 and obtain user consent information associated with the user. The consent management unit 12 is then adapted to control consent operations of the plurality of services 15 registered to the user 11, based on user consent information associated with the user 11.

The consent operations includes operations employing data privacy preference information associated with the user 11. These operations further include responding to a user request from the user 11, responding to a service request from the plurality of services 15, and/or determining if the user consent information associated with the user 11 is consistent with data access requirements of a service 15.

When responding to a user request from the user 11, the consent management unit 12 is further adapted to receive the user request from the user 11 and request the plurality of services 15 to complete the user request. The consent management unit 12 is further adapted to synchronize the user consent information between the consent management system 12 and the plurality of services 15.

The user request includes, but is not limited to, updating the user's consent, revoking the user's consent, correcting the user consent information, and/or deleting the user consent information.

When responding to a service request, the consent management unit 12 is further adapted to receive the service request from the plurality of services 15, notify the user 11 of an update, and receive a user response. The consent management unit 12 is further adapted respond to the plurality of services 15 according to the user response.

The service request includes, but is not limited to, updating a privacy notice and/or updating the user's consent.

When registering the plurality of services 15 to the user 11, the consent management unit 12 is adapted to delegate the consent management unit 12 to manage the user's consent, generate a token, then register the plurality of services 15 to the user 11 using the token.

The token includes, but is not limited to, a consent management system network address, a service network address, the user request, a timestamp; a validation period for the user consent and/or a digital signature.

Additionally, the consent management unit 12 is further adapted to receive the user consent information associated with the user 11. The consent management unit 12 is configured to be in direct communication with the plurality of services 15. For example, the consent management unit 12 is in direct communication with a consent manager of a service 15.

The user interface unit 13 is adapted to display a list of the plurality of services 15, notifications from the plurality of services 15, a list of entries of consent; and/or a list of user rights.

The user interface unit 13 is in direct communication with the consent management unit 12. For example, the user interface unit 13 is a web portal, a website, or an application interface.

The data storage unit 14 is adapted to store the user consent information associated with the user 11.

The data storage unit 14 is in direct communication with the consent management unit 12.

Figure 2:
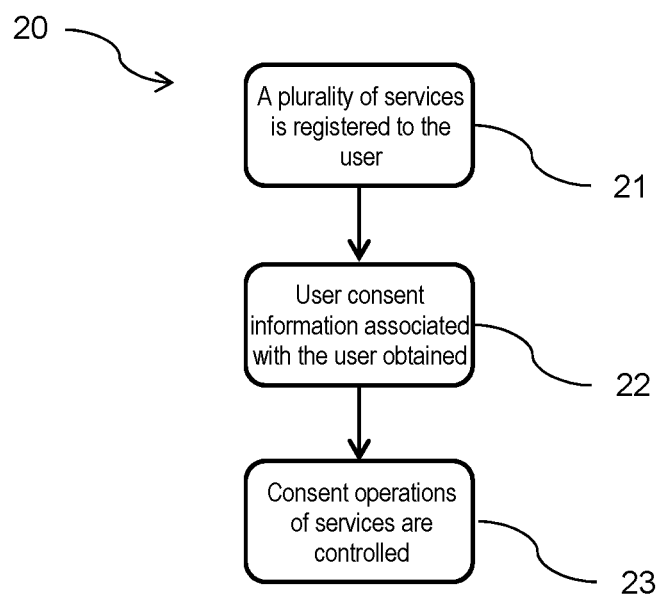
FIG. 2 is a flow-diagram of a method for managing a user's consent for the plurality of services according to an embodiment.

FIG. 2 shows a method 20 for managing a user's consent for a plurality of services 15.

The method 20 begins in step 21 where a plurality of services 15 is registered to the user 11.

In step 22, the user consent information associated with the user 11 is obtained.

In step 23, consent operations of the plurality of services 15 registered to the user 11 are controlled, based on user consent information associated with the user 11.

Figure 3:
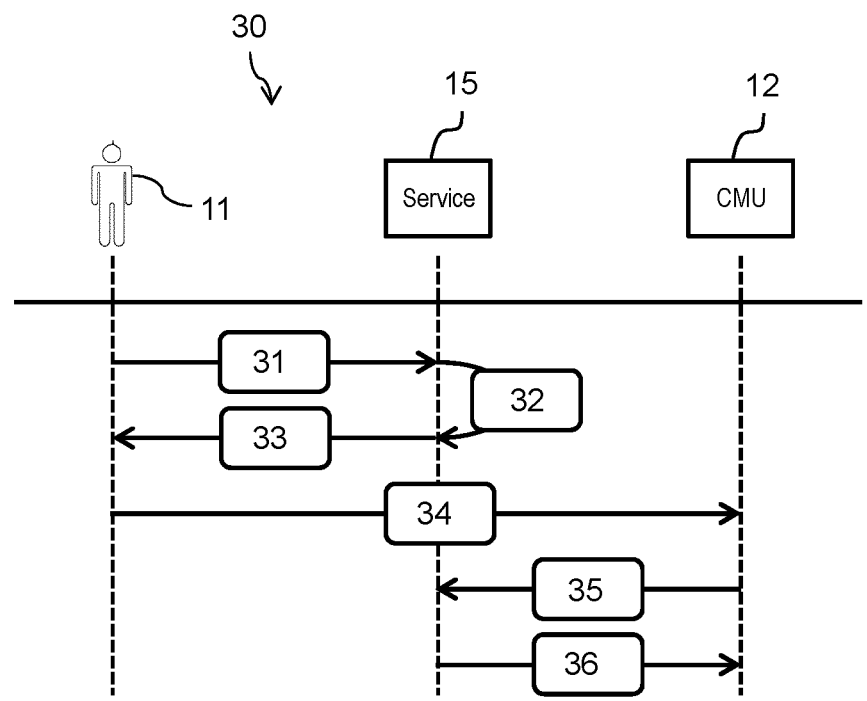
FIG. 3 shows a method for registering the plurality of services to a user according to an embodiment.

FIG. 3 shows a method 30 for registering the plurality of services 15 to the user 11, as described in step 21.

In step 31, the user 11 delegates the system 10 to manage the user's consent and corresponding user consent information at a service 15.

In step 32, a token is then generated by means of the consent management unit 12.

The token includes at least one of a consent management system network address, a service network address, a user request, a timestamp, a validation period for the user consent, and a digital signature. For example, the network addresses for the consent management system 10 and the service 15 are their respective Uniform Resource Locator (URL). The user request is the request of registering the service 15 to the user 11. The user request further records information on the user request. The timestamp provides an indication of the time that the token is generated and/or updated. The validation period for the user consent provides a date range for which the token is valid. If the token is no longer valid, the consent management unit 12 generates an updated token. The digital signature is provided by the user 11 and provides confirmation that the user 11 has acknowledged the token.

In step 33, the token is returned to the user 11 for a request of user acknowledgment of the token.

In step 34, once the user acknowledgement is confirmed and received by the consent management unit 12, the service 15 is registered with the token, by means of the consent management unit 12.

In step 35, the consent management unit 12 then provides a request containing the token to the service 15, requesting to manage the user's consent.

In step 36, the consent management unit 12 receives a response from the service 15 corresponding to the request for registration.

The consent operations of step 33 include operations employing data privacy preference information associated with the user 11. The operations employing data privacy preference information further include responding to a user request from the user 11, responding to a service request from the plurality of services 15, and/or determining if the user consent information associated with the user 11 is consistent with the data access requirements of a service 15.

In responding to a user request from the user 11, the consent management unit 12 receives the user request from the user 11 and requests the plurality of services 15 to complete the user request. The consent management unit 12 then synchronizes the user consent information between the consent management system 10 and the plurality of services 15.

Figure 4:
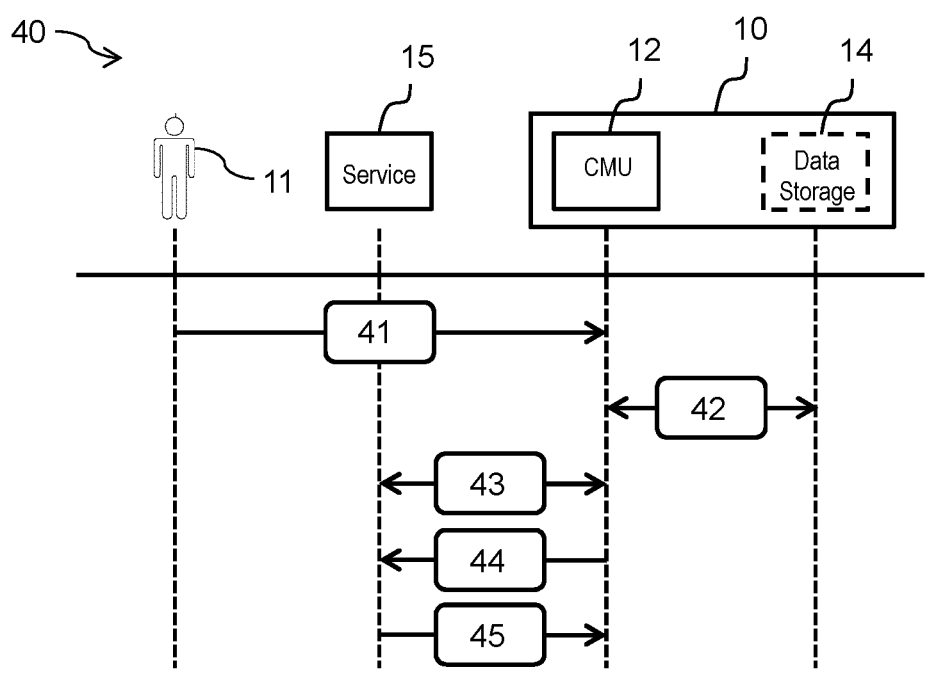
FIG. 4 shows a method for synchronizing user consent information between a consent management system and the plurality of services according to an embodiment.

FIG. 4 shows a method 40 for synchronizing the user consent information between the consent management system 10 and the plurality of services 15.

In step 41, the process is triggered by a user request for updating the user's consent. The process is also triggered when the user's consent and/or the user consent information is updated or amended.

In step 42, the consent management unit 12 receives the updated user's consent and updates the user's consent stored in the data storage unit 14 based on the received updated user's consent.

In step 43, the consent management unit 12 then provides the plurality of services 15 with the updated user's consent, for example using an authentication process. For example, the consent management unit 12 provides the updated user's consent to a database of the service 15.

In step 44, the user's request at the plurality of services 15 is then synchronized with respect to the updated user's consent. For example, the updated user's consent at a service management unit of the service 15 is synchronized with the updated user's consent at the consent management unit 12. Further, the service 15 internally synchronizes the updated user's consent between the service management unit and the database of the service 15.

In step 45, the process is completed when the consent management unit 12 receives a response from the plurality of services 15 confirming the status of the synchronization. For example, the consent management unit 12 receives the response from the service management unit.

The consent management unit 12 provides the option for the user 11 to directly contact the plurality of services or specific service with their request, for example through the user interface unit 13.

The operations employing data privacy preference information further include responding to a service request from the service 15. The service request includes, but is not limited to, updating a privacy notice and/or updating the user's consent.

Figure 5:
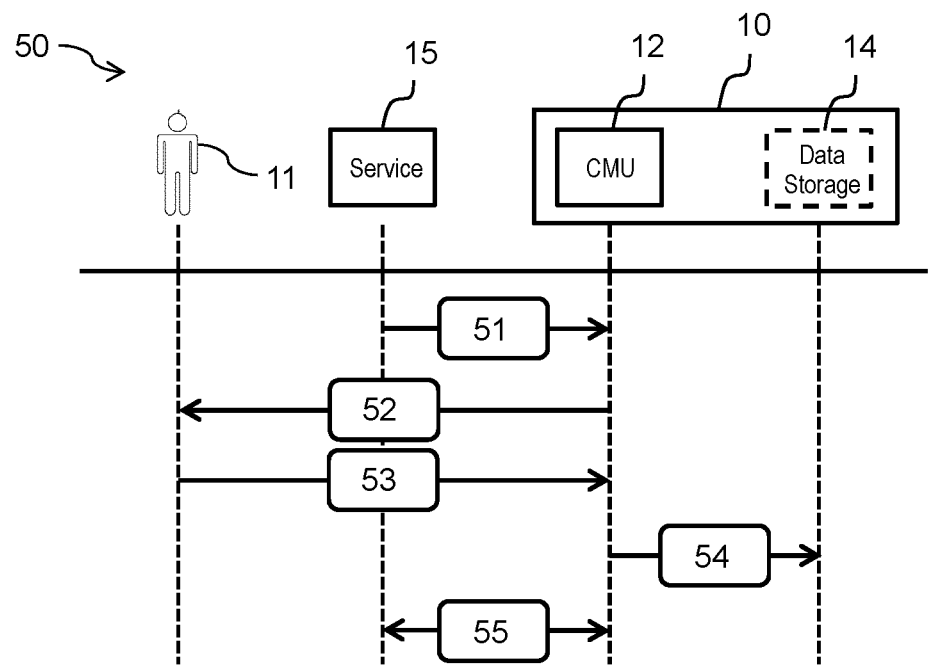
FIG. 5 shows a method for updating a privacy notice according to an embodiment.

FIG. 5 shows a method 50 for updating a privacy notice.

In step 51, the consent management unit 12 receives a privacy notice update request from the plurality of services 15.

In step 52, the consent management unit 12 notifies the user 11 of the privacy notice update, for example by providing a notification.

In step 53, the user 11 provides a response to the consent management unit 12. The response includes the updated user's consent corresponding to the privacy notice update.

In step 54, the consent management unit 12 generates and stores a backup of the updated user's consent in the data storage unit 14.

In step 55, the consent management unit 12 provides a response to the plurality of services 15. For example, the response may be provided to a service management unit. The process is completed when the consent management unit 12 receives a response to the plurality of services 15 confirming the status of the privacy notice update. The consent management unit 12 may, for example, receive the response from the service management unit.

It will be appreciated from the description above that the proposed system may employ a controller or processor for processing data.

Figure 6:
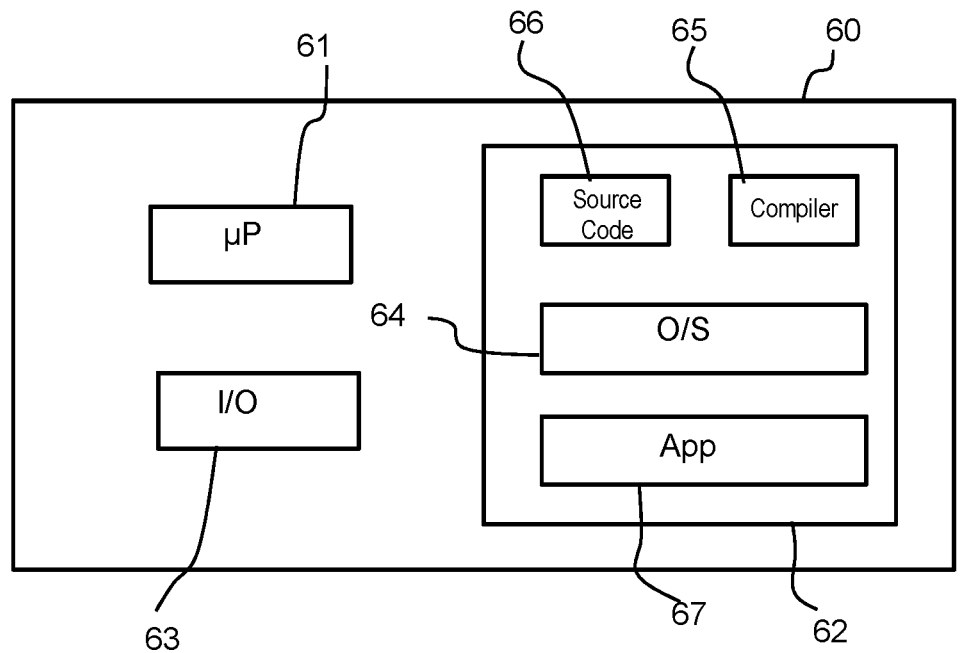
FIG. 6 illustrates an example of a computer for implementing a controller or processor according to an embodiment.

FIG. 6 illustrates an example of a computer 60 for implementing the controller or processor described above.

The computer 60 includes, but is not limited to, PCs, workstations, laptops, PDAs, palm devices, servers, storages, and the like. Generally, in terms of hardware architecture, the computer 60 may include one or more processors 61, memory 62, and one or more I/O devices 63 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 61 is a hardware device for executing software that can be stored in the memory 62. The processor 61 can be virtually any custom made or commercially available processor, a central processing unit (CPU), a digital signal processor (DSP), or an auxiliary processor among several processors associated with the computer 60, and the processor 61 may be a semiconductor based microprocessor (in the form of a microchip) or a microprocessor.

The memory 62 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 62 may incorporate electronic, magnetic, optical, and/or other types of storage media. Note that the memory 62 can have a distributed architecture, where various components are situated remote from one another, but can be accessed by the processor 61.

The software in the memory 62 may include one or more separate programs, each of which comprises an ordered listing of executable instructions for implementing logical functions. The software in the memory 62 includes a suitable operating system (O/S) 64, compiler 65, source code 66, and one or more applications 67 in accordance with exemplary embodiments.

The application 67 comprises numerous functional components such as computational units, logic, functional units, processes, operations, virtual entities, and/or modules.

The operating system 64 controls the execution of computer programs, and provides scheduling, input-output control, file and data management, memory management, and communication control and related services.

Application 67 may be a source program, executable program (object code), script, or any other entity comprising a set of instructions to be performed. When a source program, then the program is usually translated via a compiler (such as the compiler 65), assembler, interpreter, or the like, which may or may not be included within the memory 62, so as to operate properly in connection with the operating system 64. Furthermore, the application 67 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 63 may include input devices such as, for example but not limited to, a mouse, keyboard, scanner, microphone, camera, etc. Furthermore, the I/O devices 63 may also include output devices, for example but not limited to a printer, display, etc. Finally, the I/O devices 63 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 63 also include components for communicating over various networks, such as the Internet or intranet.

When the computer 60 is in operation, the processor 61 is configured to execute software stored within the memory 62, to communicate data to and from the memory 62, and to generally control operations of the computer 60 pursuant to the software. The application 67 and the operating system 64 are read, in whole or in part, by the processor 61, perhaps buffered within the processor 61, and then executed.

When the application 67 is implemented in software it should be noted that the application 67 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The system 10 may be a blockchain-based consent management system. The block-chain based system may be adapted to record user consent information, a privacy notice from the plurality of services 15, a user request, and/or a service request.

In an embodiment, the user request may be a request to revoke the user's consent. In order to revoke the user's consent, the user 12 may access the consent management system 10, for example using the user interface unit 13. The user 11 may then request to revoke the user's consent for the plurality of services 15 or a specific service 15. The consent management unit 12 may then provide the request to the plurality of services 15 or the specific service 15.

In a further embodiment, the user request may be a request to correct user consent information. In order to correct the user consent information, the user 12 may access the consent management system 10, for example using the user interface unit 13. The user 11 may then request to correct the user consent information for the plurality of services 15 or a specific service 15. The consent management unit 12 may then provide the request to the plurality of services 15 or the specific service 15. For example, the system 10 is used as an auditing platform for correcting user consent information.

In a further embodiment, the user request may be a request to delete user consent information. In order to delete the user consent information, the user 12 may access the consent management system 10, for example using the user interface unit 13. The user 11 may then request to delete the user consent information for the plurality of services 15 or a specific service 15. The consent management unit 12 may then provide the request to the plurality of services 15 or the specific service 15.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A consent management system for managing a user's consent for a plurality of medical services, the system comprising:
   one or more processors; and
   a memory storing at least a consent management unit;
      wherein the consent management unit is adapted to:
      register a plurality of medical services to a user;
      obtain user consent information associated with the user; and
      control consent operations of the plurality of medical services registered to the user, based on user consent information associated with the user, wherein the consent operations comprise operations employing data privacy preference information associated with the user;
   wherein the consent operations include responding to a medical service request from a first medical service of the plurality of medical services, the medical service request comprising one or more of updating a privacy notice and updating the user's consent; and
   wherein in responding to the medical service request, the consent management unit is further adapted to:
      receive the medical service request from the first medical service of the plurality of medical services;
      in response to the medical service request received from the first medical service, notify, via the consent management unit, the user of updates from multiple medical services of the plurality of medical services, wherein the updates from the multiple medical services include updates to one or more service-specific privacy notices;
      receive, via the consent management unit, a user response; and respond to at least the first medical service of the plurality of medical services according to the user response.

2. The system of claim 1, wherein the consent operations employing data privacy preference information comprise at least one of:
   responding to a user request from the user; and
   determining if the user consent information associated with the user is consistent with data access requirements of a medical service.

3. The system of claim 2, wherein in responding to a user request from the user, the consent management unit is adapted to:
   receive the user request from the user;
   request the plurality of medical services to complete the user request; and
   synchronize the user consent information between the consent management system and the plurality of medical services.

4. The system of claim 2, wherein the user request comprises one or more of:
   updating the user's consent;
   revoking the user's consent;
   correcting the user consent information; and
   deleting the user consent information.

5. The system of claim 1, wherein the memory of the system further comprises a data storage unit adapted to store the user consent information associated with the user.

6. The system of claim 1, wherein in registering the plurality of medical services to the user, the consent management unit is adapted to:
   delegate the consent management unit to manage the user's consent;
   generate a token; and
   register the plurality of services to the user using the token.

7. The system of claim 6, wherein the token comprises at least one of: a consent management system network address; a service network address; the user request; a timestamp; a validation period for the user consent; and a digital signature.

8. The system of claim 1, wherein the memory of the system further comprises a user interface unit adapted to display, on a display, one or more of:
   a list of the plurality of medical services;
   notifications from the plurality of medical services;
   a list of entries of consent; and
   a list of user rights.

9. The system of claims 8, wherein the system is a blockchain-based consent management system adapted to record one or more of:
   the user consent information;
   the privacy notice from the plurality of medical services;
   the user request; and
   the service request.

10. The system of claim 1, wherein the consent management unit is further adapted to receive the user consent information.

11. A method for managing a user's consent for a plurality of medical services, the method comprising:
   registering a plurality of medical services to the user;
   obtaining user consent information associated with the user; and
   controlling consent operations of the plurality of medical services registered to the user, based on user consent information associated with the user, wherein the consent operations comprise operations employing data privacy preference information associated with the user;
   wherein controlling the consent operations includes responding to a medical service request from a first medical service of the plurality of medical services by:
      receiving, at the consent management unit, the medical service request from the first medical service of the plurality of medical services, the medical service request comprising one or more of updating a privacy notice and updating the user's consent;
      in response to the medical service request received from the first medical service, notifying, via the consent management unit, the user of updates from multiple medical services of the plurality of medical services, wherein the updates from the multiple medical services include updates to one or more service-specific privacy notices;
      receiving, via the consent management unit, a user response; and
   responding, from the consent management unit, to at least the first medical service of the plurality of medical services according to the user response.

* * * * *